United States Patent [19]

Blewett et al.

[11] Patent Number: 4,496,758

[45] Date of Patent: Jan. 29, 1985

[54] PROCESS FOR THE METATHESIS OF ALKENYL ESTERS

[75] Inventors: Charles W. Blewett, Fort Mitchell, Ky.; Michael D. Sublett, Cincinnati, Ohio

[73] Assignee: National Distillers and Chemical Corporation, New York, N.Y.

[21] Appl. No.: 541,757

[22] Filed: Oct. 13, 1983

[51] Int. Cl.³ .............................................. C07C 69/76
[52] U.S. Cl. .................... 560/112; 560/113; 560/262; 260/405; 260/408; 260/410.5; 260/410.6; 260/410.9 N
[58] Field of Search ...................... 560/112, 113, 262; 260/405, 408, 410.5, 410.6, 410.9

[56] References Cited
U.S. PATENT DOCUMENTS 4,233,230  11/1980  Otton ................................. 560/113

Primary Examiner—Paul J. Killos
Attorney, Agent, or Firm—Kenneth D. Tremain; Gerald A. Baracka

[57] ABSTRACT

An improved process for the metathesis of alkenyl esters utilizing substantially reduced catalyst levels is provided. For the process, an alkenyl ester of the formula

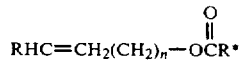

where R is hydrogen or alkyl, R* is tertiary alkyl or an aromatic group, and n is an integer from 2 to 20 is reacted with a tungsten hexachloride/tetraalkyltin catalyst.

26 Claims, No Drawings

PROCESS FOR THE METATHESIS OF ALKENYL ESTERS

BACKGROUND OF THE INVENTION

1. Field of the Invention

The present invention relates to a process for the metathesis of alkenyl esters utilizing a homogeneous catalyst comprised of tungsten hexachloride and a tetraalkyltin.

2. Description of the Prior Art

Metathesis reactions using functionalized olefins have been the subject of considerable research since the discovery by van Dam et al. that methyl oleate can be metathesized into 9-octadecene and dimethyl 9-octadecenedioate (see *J. Chem. Soc. Chem. Comm.*, 1221 (1972)). Using the homogeneous catalyst $WCl_6/Sn(Me)_4$, van Dam et al. reported a conversion of about 50 percent in two hours at 100° C. and reactant-:catalyst ratio of 75:1. Similar results were reported by van Dam et al. with methyl elaidate, methyl erucate, methyl undecenate, methyl linoleate and methyl linolenate. Nakamura, in *Petrotech*, 4, 623 (1981), also reported the metathesis and co-metathesis of methyl esters of unsaturated acids using catalysts based on tungsten hexachloride and other transition metals.

In addition to the metathesis of unsaturated esters wherein the unsaturation is present in the acyl moiety of the molecule, metathesis of alkenyl esters of monocarboxylic acids, i.e., esters wherein the unsaturation is located in the alcohol-derived moiety, using tungsten catalysts is also known. For example, Tsuji et al. (*J. Organomet. Chem.*, 218, 69–80 (1981)) have metathesized oleyl acetate to obtain 9-octadecene and 1,18-diacetoxy-9-octadecene using $WCl_6$ or $WOCl_4$ as the primary catalyst with $SnMe_4$, $Cp_2TiMe_2$ or $Cp_2TiClMe$ as co-catalyst. Similarly, 4-acetoxy-1-butane, 5-acetoxy-1-pentene and 6-acetoxy-1-hexene were cross metathesized with 2-hexene and cyclooctene using $WCl_6/Sn(Me)_4$ catalyst by Otton et al., (*J. Mol. Catal.*, 8, 313–324 (1980)). J. C. Mol (*Chemtech*, April 1983, 250–255) metathesized esters with a double bond in the alcohol fragment (alkenyl esters) to produce ethylene and the corresponding α,Ω-diacetoxyalkene. Specifically, Mol reacted $CH_2=CH(CH_2)_nOOCCH_3$, where n=2, 3 or 8, at 70° C. using a $WCl_6/Sn(Me)_4$ catalyst at a molar ratio (ester:$WCl_6$) of 10:1. Conversions of 41–45 percent with selectivities of 88–95 percent to the desired $CH_3COO(CH_2)_nHC=CH(CH_2)_nOOCCH_3$ were obtained.

With all of the above reactions involving alkenyl esters, very high catalyst levels are required. Molar ratios (ester:$WCl_6$) of about 10:1 (10 mole percent) are typically required and, in some instances, 20 mole percent catalyst (ester:$WCl_6$ ratio of 5:1) is necessary to achieve acceptable rates of reaction and conversion. Also, all of the prior art metathesis reactions involving alkenyl esters have utilized acetate esters.

It would be highly desirable if a process were available whereby alkenyl esters could be metathesized utilizing significantly lower levels of the costly tungsten hexachloride catalyst. It would be even more advantageous if acceptable reaction rates with high conversion of the alkenyl ester and high selectivity to the desired metathesis products were obtained.

SUMMARY OF THE INVENTION

We have now quite unexpectedly discovered an improved process for the metathesis of alkenyl esters whereby rapid rates of reaction with good conversion of the alkenyl ester and high selectivity to the desired product are obtained at low catalyst levels. Whereas 10–20 mole percent tungsten hexachloride, based on the alkenyl ester, is required for the prior art processes, with the process of this invention it is possible to obtain acceptable results, in some cases superior to those heretofore reported, at catalyst levels of 1 mole percent or below. It is totally unexpected and surprising that metathesis will occur at such drastically reduced catalyst levels in view of the recognized poisoning effect of the polar ester moiety. As a result of the favorable economics of the process, due to the small amount of catalyst required, the metathesis of alkenyl esters on a commercial basis is now possible.

The process of this invention involves contacting an alkenyl ester, alone or in combination with an alkene, with a tungsten hexachloride/tetraalkyltin catalyst at a temperature from 0° C. to 200° C., said tungsten hexachloride present in an amount from 0.1 to 5 mole percent, based on the alkenyl ester, and the molar ratio of tetraalkyltin to tungsten hexachloride ranging from 0.4:1 to 6:1. A nitrogeneous or trivalent phosphorous modifying agent may be employed with the tungsten hexachloride and tetraalkyltin at a mole ratio (modifier:$WCl_6$) of 0.01:1 to 0.75:1. Alkenyl esters employed for the process have the formula

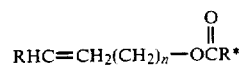
$$RHC=CH_2(CH_2)_n-OCR^*$$

where R is hydrogen or an alkyl group having from 1 to 10 carbon atoms, n is an integer from 2 to 20 and R* is (a) a tertiary alkyl group having from 4 to 20 carbon atoms of the formula

where $R_1$, $R_2$ and $R_3$ represent the same or different alkyl groups having from 1 to 9 carbon atoms, or (b) an aromatic group of the formula

where $R_4$ and $R_5$ are hydrogen, halo or an alkyl group having from 1 to 8 carbon atoms. Especially useful alkenyl esters have from 4 to 22 carbon atoms in the alkenyl moiety with R* being a tertiary alkyl group containing from 4 to 9 carbon atoms or an aromatic moiety where $R_5$ is hydrogen and $R_4$ is hydrogen, chloro, bromo, or a $C_{1-4}$ alkyl group.

Alkenes which can be present with the alkenyl ester contain from 3 to 50 carbon atoms and correspond to the formula

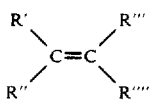

where R' is an alkyl group having from 1 to 40 carbon atoms, a $C_{3-6}$ cycloalkyl alkyl-substituted cycloalkyl having from 4 to 20 carbon atoms, phenyl or alkyl-substituted phenyl having from 7 to 20 carbon atoms or a radical of the formula

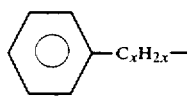

where X is an integer from 1 to 20, R'', R''' and R'''' are hydrogen or a radical as defined for R'. α-Olefins are especially useful alkenes.

In a preferred embodiment of this invention, an Ω-alkenyl ester wherein R is hydrogen and n is an integer from 6 to 16 is reacted at a temperature of 50° C. to 150° C. utilizing 0.25 to 3 mole percent tungsten hexachloride. It is even more preferable if the reaction is carried out using a $(C_{1-4}$ alkyl$)_4$Sn compound and pyridine modifier.

DETAILED DESCRIPTION

For the process of this invention an alkenyl ester is metathesized utilizing a homogeneous catalyst comprised of tungsten hexachloride and a tetraalkyltin compound. Alkenyl esters employed for the metathesis correspond to the general formula

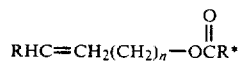

where R is hydrogen or an alkyl group having from 1 to 10 carbon atoms, n is an integer from 2 to 20 and R* is (a) a tertiary alkyl group of the formula

where $R_1$, $R_2$ and $R_3$ represent the same or different alkyl groups having from 1 to 9 carbon atoms, with the proviso that the total number of carbon atoms in the group is 4 to 12, or (b) a phenyl or substituted-phenyl group of the formula

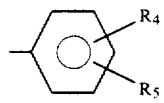

where $R_4$ and $R_5$ are, independently, hydrogen, halo or an alkyl group having from 1 to 8 carbon atoms.

Preferably, the total number of carbon atoms in the alkenyl moiety $RHC=CH_2(CH_2)_n-$ is from 4 to 22 and, in a particularly useful embodiment of this invention, the alkenyl group is an Ω-alkenyl radical, i.e., R=H, with n being an integer from about 6 to 16. The tertiary alkyl group (a) preferably contains from 4 to 9 carbon atoms and it is particularly advantageous if $R_1$, $R_2$ and $R_3$ are methyl groups. Preferred phenyl or substituted-phenyl radicals (b) have $R_4=H$, chloro, bromo or $C_{1-4}$ alkyl and $R_5=H$.

The alkenyl esters are readily obtained by the reaction of an unsaturated alcohol of the formula $RHC=CH_2(CH_2)_nOH$ with a neo-acid of the formula

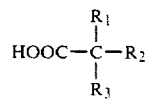

or aromatic acid of the formula

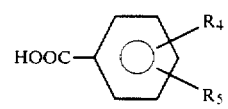

where R, $R_1$, $R_2$, $R_3$, $R_4$, $R_5$ and n are the same as defined above. Representative of the alcohols which can be employed to obtain the alkenyl esters useful in the process are oleyl alcohol, erucyl alcohol, 10-undecenyl alcohol, 11-dodecenyl alcohol, 8-nonenyl alcohol, cis-3-hexenol, trans-3-hexenol, 9-decenyl alcohol, 5-hexenyl alcohol, 6-heptenyl alcohol, 7-octenyl alcohol, 4-octenyl alcohol, 4-pentenyl alcohol, 3-butenyl alcohol, cis-2-hexenyl alcohol, trans-2-hexenyl alcohol, trans-3-octenyl alcohol, cis-3-octenyl alcohol, cis-4-decen-1-ol, cis-4-hepten-1-ol, cis-3-nonen-1-ol, cis-6-nonen-1-ol, cis-3-octen-1-ol, cis-5-octen-1-ol, and the like. In addition to primary alcohols, alkenyl esters useful in the process may also be obtained from secondary alcohols.

Neo-acids which can be reacted with the above-defined unsaturated alcohols include 2,2-dimethylpropanoic acid (trimethylacetic acid; pivalic acid, neopentanoic acid), 2,2-dimethylbutanoic acid, 2,2-dimethylpentanoic acid, 2,2-dimethylheptanoic acid, 4-ethyl-2,2-dimethyloctanoic acid, 2,2-dimethyldecanoic acid, commercially available acids which consist primarily of $C_{10}$ tertiary acids or mixtures of $C_{9-11}$ tertiary acids, and the like.

Aromatic acids which can be employed to obtain the alkenyl esters used in the process include, most notably, benzoic acid, 2-, 3- or 4-chlorobenzoic acid, 2- , 3- or 4-bromobenzoic acid, 2,4-dibromobenzoic acid, 2,6-dichlorobenzoic acid, 4-methylbenzoic acid, 4-ethylbenzoic acid, 4-t-butylbenzoic acid, 2,4-dimethylbenzoic acid, 2,6-dimethylbenzoic acid, and the like. Esters of tri- and higher-substituted benzoic acids may also be employed.

In accordance with one of the preferred embodiments of the invention which utilizes an Ω-alkenyl ester such as defined above, the metathesis reaction is described by the following equation

where R* and n are the same as defined above.

As noted from the equation two products are obtained from the reaction. However, since ethylene is vented from the system during the reaction, recovery of the diester product is facilitated. Removal of the ethylene also shifts the equilibrium, favoring high conversion of the alkenyl ester and optimizing the yield of the diester. Diester is easily separated from any unreacted Ω-alkenyl ester by distillation or recrystallization due to the significant difference in the molecular weights. Reactions of this type provide a convenient and economical route to unsaturated diesters which can be utilized as such for the production of polyesters, polyamides, etc. or further reacted to obtain sex phermones. Hydrolysis of the ester will provide the corresponding α,Ω-dihydroxy material which in turn can be selectively reduced to obtain a long-chain alkene. Long-chain alkenes have recognized utility as sex phermones. For example, cis-9-tricosene is a known sex attractant for the common house fly.

It is also possible to cross-metathesize the above-defined alkenyl ester with other alkenes. Alkenes useful for co-metathesis with the alkenyl esters include olefinic hydrocarbons having from 3 up to about 50 carbon atoms and corresponding to the general formula

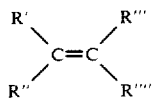

where R' is an alkyl group having from 1 to 40 carbon atoms, $C_{3-6}$ cycloalkyl or alkyl-substituted cycloalkyl having from 4 to 20 carbon atoms, phenyl or alkyl-substituted phenyl having from 7 to 20 carbon atoms or radical of the formula

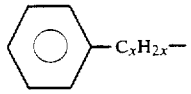

where x is an integer from 1 to 20, and R'', R''' and R'''' are, independently, hydrogen or a radical as defined above for R'. For such reactions, a pure olefin may be employed or a mixture of olefins, which can be the same or different types, can be utilized. Additionally, cyclic olefins such as cyclohexene and cyclooctene can be employed.

α-Olefins where R'', R''' and R'''' are hydrogen and R' is an alkyl group having from 1 to 30 and, more preferably, 4 to 16, carbon atoms are particularly advantageous for cross-metathesis with the alkenyl esters. Suitable α-olefins include, but are not limited to, propylene, 1-butene, 1-pentene, 1-hexene, 1-octene, 1-nonene, 1-decene, 1-dodecene, 1-tetradecene and the like. Utilizing an Ω-alkenyl ester and α-olefin, the co-metathesis reaction is represented by the equation

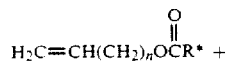

-continued

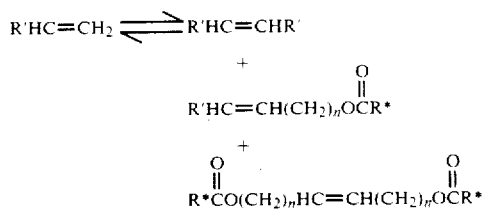

where R*, R' and n are the same as defined above. It is possible to obtain a variety of useful products by such reactions. For example, in accordance with the above equation an 11-dodecenyl ester can be cross-metathesized with 1-eicosene to yield as the principle component an 11-triacontenyl ester which, after separation from the other components, can be hydrolyzed and reduced to obtain 1-triacontanol, a known growth promoter.

Tungsten hexachloride is employed as the catalyst in conjunction with a tetraalkyltin compound, for the metathesis and co-metathesis reactions. While small amounts of tungsten oxyhalides may be present with the tungsten hexachloride, it is preferable to keep the level of tungsten oxy-compounds to as low a level as possible for optimum results. For this reason, it is sometimes advantageous to purify the tungsten hexachloride prior to use. This is readily accomplished by heating the tungsten hexachloride at 200° C. under a constant flow of nitrogen for about two hours.

Tetraalkyltin compounds useful as co-catalytic agents with the tungsten hexachloride have the general formula

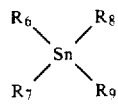

where $R_6$, $R_7$, $R_8$ and $R_9$ are, independently, an alkyl group containing from 1 to 12 carbon atoms. Tetraalkyltin compounds of the above type include tetramethyltin, dimethyldiethyltin, tetraethyltin, diethyldibutyltin, tetrabutyltin, tetraoctyltin, and the like. Especially useful tetraalkyltin compounds, in view of their commercial availability, are tetraalkyltin compounds wherein the alkyl groups ($R_6$, $R_7$, $R_8$ and $R_9$) contain from 1 to 4 carbon atoms. Organotin compounds wherein one or more of the alkyl groups is replaced with a cycloalkyl, phenyl or alkyl-substituted phenyl and benzyl or alkyl-substituted benzyl group may also be used as a co-catalyst with the tungsten hexachloride. The molar ratio of the tetraalkyltin compound to tungsten hexachloride can range from about 0.4:1 to 6:1, however, catalyst systems wherein the molar ratio is 1:1 to 4:1 are particularly advantageous.

Known nitrogeneous and trivalent phosphorous modifying agents, such as those disclosed in U.S. Pat. Nos. 4,078,012 and 4,078,013—the teachings of which are incorporated herein, can also be present with the tungsten hexachloride and tetraalkyltin compound. While such modifying agents are not necessary for the process, they can be advantageous depending on the particular reactants and reaction conditions employed. When a modifier is employed, it will generally be present at a mole ratio of 0.01:1 to 0.75:1 (modifier:$WCl_6$). In an especially useful embodiment of this invention pyridine is used as the modifier at a molar ratio (pyridine:WCl$_6$) of 0.1:1 to 0.5:1.

The process can be conducted over a wide range of temperatures from about 0° C. up to about 220° C. but, most generally, the reaction temperature will range from 50° C. to 150° C. Operating pressures can vary from sub-atmospheric to super-atmospheric and the pressure will generally be governed by the reactants and other operating conditions. Whenever possible, the reaction is conducted at atmospheric pressure or as close thereto as possible. An inert atmosphere of nitrogen, argon or helium is generally employed and precautions are taken to exclude moisture from the system. While solvents are not necessary for the reaction, an inert hydrocarbon diluent such as benzene, toluene, xylene, cyclohexane, methylcyclohexane, pentane, hexane, isooctane, or other inert aromatic, paraffinic or cycloparaffinic hydrocarbons can be employed.

As has been previously pointed out, one of the primary advantages of the present process if the ability to metathesize or co-metathesize alkenyl esters utilizing catalyst levels which were heretofore not possible. Whereas prior art processes required 10 to 20 mole percent tungsten hexachloride, i.e., a mole ratio of alkenyl ester to WCl$_6$ of 5–10:1, quite unexpectedly with the process of this invention it is possible to obtain rapid and high conversion of the alkenyl ester with good selectivity to the desired product at significantly lower catalyst levels. For the present process, the mole percent of tungsten hexachloride, based on the alkenyl ester, is generally less than 5 and may be as low as 0.1. While larger amounts of catalyst can be employed, this is generally not desirable due to the additional catalyst cost and decrease in selectivity of the reaction. It is particularly advantageous to employ 0.25 to 3 mole percent tungsten hexachloride based on the alkenyl ester. In view of the ability to obtain high conversions with good selectivity to the desired product at low tungsten hexachloride levels, the economics of the reaction are favorable for commercial operation.

In a typical batch-type metathesis, the tungsten hexachloride is combined with the alkenyl ester and the mixture heated to the desired temperature under a nitrogen atmosphere. After stirring for a short period of time, the tetraalkyltin compound and any modifying agent is charged to the reactor. If an Ω-alkenyl ester is employed, evolution of ethylene occurs almost immediately. While equilibrium is generally reached after about only 15 minutes (as determined by the amount of ethylene evolved), the reaction is continued for a total of about two hours. The reaction mixture is then filtered through a suitable filtering medium and the metathesis product recovered.

The following examples illustrate the invention more fully. Parts and percentages in the examples are on a weight basis unless otherwise indicated.

EXAMPLE I

Freshly sublimed tungsten hexachloride (0.59 gram; 1.5 mmole) was weighed into a dry glass reactor under an atmosphere of nitrogen and 38.1 grams (0.15 mole) 10-undecenyl pivalate added (mole ratio 10-undecenyl pivalate to WCl$_6$ of 100:1). The solution was heated to 90° C. under nitrogen with stirring and 1.56 grams (4.5 mmole) tetrabutyltin added (mole ratio tetrabutyltin to WCl$_6$ of 3:1). Evolution of ethylene was observed almost immediately. Heating and stirring were continued for two hours—after which time ethylene evolution was no longer evident. The reaction mixture was then filtered through a diatomaceous earth filter bed. Analysis of the filtrate indicated 76.1 percent conversion of the 10-undecenyl pivalate with 87.6 percent selectivity to the desired 1,20-dipivaloxy-10-eicosene product. This represents a yield of 66.7 percent 1,20-dipivaloxy-10-eicosene.

EXAMPLE II

The procedure of Example I was identically repeated except that the reaction was carried out at a temperature of 120° C. The conversion of 10-undecenyl pivalate was 68.7 percent with 86.7 percent selectivity to the desired 1,20-dipivaloxy-10-eicosene.

EXAMPLE III

To demonstrate the ability to use a modifier with the tungsten hexachloride and tetrabutyltin, the following experiment was conducted. Freshly sublimed tungsten hexachloride (0.59 gram; 1.5 mmole) was weighed into a dry glass reactor under an atmosphere of nitrogen and 38.1 grams (0.15 mole) 10-undecenyl pivalate added (mole ratio 10-undecenyl pivalate to WCl$_6$ of 100:1). The solution was heated to 120° C. and 0.03 gram pyridine (mole ratio pyridine to WCl$_6$ of 0.25:1) added with stirring. After five minutes, 1.56 grams (4.5 mmole) tetrabutyltin was charged and the reaction mixture heated at 120° C. with stirring for two hours. After filtering through a bed of diatomaceous earth, chromatographic analysis indicated 76.7 percent conversion of the 10-undecenyl pivalate with 84.0 percent selectivity to the desired 1,20-dipivaloxy-10-eicosene. This represents a yield of 1,20-dipivaloxy-10-eicosene of 64.4 percent.

EXAMPLES IV–VII

The ability to vary the amount of tungsten hexachloride and reaction temperature was demonstrated by the following series of experiments conducted in accordance with the procedure of Example III. Details of the experiments including percent conversion of the 10-undecenyl pivalate and percent yield 1,20-dipivaloxy-10-eicosene were as follow:

|  | Ex. IV | Ex. V | Ex. VI | Ex. VII |
|---|---|---|---|---|
| Reaction Temperature (°C.) | 90 | 105 | 120 | 120 |
| 10-Undecenyl Pivalate (gms) | 38.1 | 38.1 | 38.1 | 38.1 |
| Tungsten Hexachloride (gms) | 0.59 | 0.59 | 0.59 | 0.40 |
| Mole Ratio 10-Undecenyl Pivalate:WCl$_6$ | 100:1 | 100:1 | 100:1 | 150:1 |
| Tetrabutyltin (gms) | 1.56 | 1.56 | 1.56 | 1.09 |
| Pyridine (gms) | 0.03 | 0.03 | 0.03 | 0.02 |
| % Conversion | 65.4 | 71.4 | 76.1 | 63.2 |
| % Yield | 61.3 | 63.5 | 59.4 | 58.8 |

EXAMPLE VIII

To demonstrate the ability to carry out the metathesis at even lower catalyst levels, a mole ratio of 10-undecenyl pivalate to tungsten hexachloride of 300:1 was employed. For the reaction, 38.1 grams 10-undecenyl pivalate, 0.20 gram tungsten hexachloride, 0.52 gram tetrabutyltin and 0.01 gram pyridine were charged and the reaction carried out at 90° C. While conversion of 10-undecenyl pivalate was only 16.3 percent after two hours, selectivity to the desired 1,20-dipivaloxy-10-eicosene was 90.6 percent. Continuing the reaction for an additional period improved the conversion without significantly changing the selectivity.

EXAMPLE IX

The versatility of the process is demonstrated by the following example wherein 10-undecenyl benzoate was metathesized in accordance with the general procedure of Example I. For the reaction 0.58 gram (1.46 mmole) freshly sublimed tungsten hexachloride was charged to a dry reactor under an atmosphere of nitrogen followed by the addition of 50 grams (0.182 mole) 10-undecenyl benzoate (mole ratio 10-undecenyl benzoate to $WCl_6$ of 125:1). The solution was heated to 100° C. under nitrogen while stirring and 0.52 gram (2.92 mmole) tetramethyltin (mole ratio tetramethyltin to $WCl_6$ of 2:1) added. The reaction mixture was heated with stirring for two hours and worked up in the usual manner. Analysis of the resulting product indicated 42.2 percent conversion of the 10-undecenyl benzoate with 99 percent selectivity to the desired 1,20-dibenzooxy-10-eicosene. This represents a yield of 41 percent 1,20-dibenzooxy 10-eicosene.

EXAMPLE X

10-Undecenyl benzoate was metathesized as follows: 0.40 Gram (1.0 mmole) tungsten hexachloride was charged to the reactor with 37.44 grams (0.1366 mole) 10-undecenyl benzoate (mole ratio 10-undecenyl benzoate to $WCl_6$ of 136.6:1). The solution was stirred and heated under a nitrogen atmosphere to 90° C. and 0.02 gram pyridine added. After five minutes, tetrabutyltin (1.04 grams; 3.0 mmole) was added. After two hours, 44.1 percent conversion of the 10-undecenyl benzoate was obtained with 85.7 percent selectivity to the desired 1,20-dibenzooxy-10-eicosene.

EXAMPLE XI

Example X was repeated except that the amount of tungsten hexachloride was reduced even further (mole ratio 10-undecenyl benzoate:tungsten hexachloride 410:1). After two hours of reaction at 90° C., 16.1 percent conversion of the 10-undecenyl benzoate was obtained. By additional reaction it was possible to increase the conversion of the 10-undecenyl benzoate. Selectivity of the reaction to the desired 1,20-dibenzooxy-10-eicosene was 80 percent.

EXAMPLE XII

Following the general procedure of Example X, 10-undecenyl p-chlorobenzoate (22.6 grams) was metathesized by heating at 90° C. in the presence of a catalyst comprised of 0.30 gram tungsten hexachloride and 0.78 gram tetrabutyltin. Pyridine (0.01 gram) was included as a catalyst modifier. After two hours 73.4 percent conversion of the 10-undecenyl p-chlorobenzoate was achieved. The yield of 1,20-bis(p-chlorobenzooxy)-10-eicosene was 71.6 percent.

EXAMPLE XIII

Similar to Example XII, 10-undecenyl para-t-butylbenzoate (33.1 grams) was metathesized by heating at 90° C. in the presence of 0.40 gram tungsten hexachloride, 1.04 grams tetrabutyltin and 0.02 gram pyridine. After two hours, 56.5 percent conversion of the 10-undecenyl para-t-butylbenzoate was obtained with 91 percent selectivity to the desired diester product, 1,20-bis(para-t-butylbenzooxy)-10-eicosene.

EXAMPLE XIV

To demonstrate the unobviousness of the process and the criticality of the alkenyl ester, comparative reactions were conducted. Three separate reactions were carried out at 90° C. under identical conditions except that different alkenyl esters were used for each. For the first, reaction A, 10-undecenyl pivalate was used and for the second, reaction B, the alkenyl ester was 10-undecenyl benzoate. The third reaction (C) was conducted using 10-undecenyl acetate, an ester used in the prior art for metathesis reactions. For each reaction the mole ratio of alkenyl ester to tungsten hexachloride was 100:1 and the mole ratio of tetrabutyltin to tungsten hexachloride was 3:1. Pyridine was employed as a modifier for all the reactions at a mole ratio of 0.25:1 (pyridine:$WCl_6$). After two hours, reactions A and B respectively gave 77.0 and 77.8 percent conversion of the alkenyl ester whereas none of the 10-undecenyl acetate was reacted. Furthermore, reactions A and B respectively afforded 67.1 percent and 71.3 percent yields of the corresponding diester products. It is evident from the foregoing data that high conversion with good selectivity to the corresponding diester product is obtained with the pivalate and benzoate esters while no reaction is obtained with the acetate ester at the same catalyst level.

EXAMPLE XV

The versatility of the improved metathesis process of this invention is further apparent from the following example wherein 10-undecenyl pivalate and 1-eicosene were cross-metathesized. For the reaction 28.0 grams (0.1 mole) eicosene and 25.4 grams (0.1 mole) 10-undecenyl pivalate were charged to a reactor and the system purged with nitrogen. Tungsten hexachloride (0.63 gram; 1.6 mmole) was added and the mixture heated to 130° C. with stirring. Upon the addition of tetrabutyltin (1.67 grams; 4.5 mmole) evolution of ethylene was observed. The reaction was continued for two hours after which time the resulting reaction mixture was filtered through diatomaceous earth and chromatographically analyzed. Sixty-six percent conversion was obtained with 86.2 percent selectivity to the products

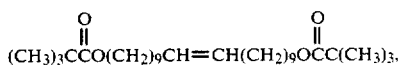

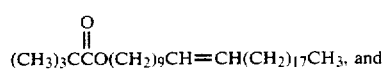

which were present at a weight ratio of 1:2.2:1.1.

EXAMPLE XVI

Example XV was repeated except that pyridine was employed as a modifier with the tungsten hexachloride and tetrabutyltin. The pyridine (0.04 gram) was added after introduction of the tungsten hexachloride (0.79 gram) and after the temperature of the solution was 130° C. The mole ratio of 10-undecenyl pivalate to tungsten hexachloride was 200:1. The mixture was then allowed to stir for five minutes before the tetrabutyltin (2.08 grams) was charged. 75.1 Percent conversion was obtained after two hours with a selectivity of 81.2 percent.

The product distribution was essentially the same as obtained without the pyridine modifier.

EXAMPLES XVII-XXI

Variations in the cross-metathesis of 10-undecenyl pivalate and 1-eicosene are evident from the following series of experiments which were conducted in accordance with the procedure of Example XVI. Experimental details including percent conversion and percent selectivity were as follows:

|  | EX. XVII | EX. XVIII | EX. XIX | EX. XX | EX. XXI |
|---|---|---|---|---|---|
| Reaction Temperature (°C.) | 120 | 140 | 130 | 120 | 140 |
| 10-Undecenyl Pivalate (gms) | 25.4 | 25.4 | 25.4 | 25.4 | 25.4 |
| 1-Eicosene (gms) | 28.0 | 28.0 | 28.0 | 28.0 | 28.0 |
| Tungsten Hexachloride (gms) | 0.79 | 0.79 | 0.63 | 0.53 | 0.53 |
| Mole Ratio 10-Undecenyl Pivalate:WCl$_6$ | 100:1 | 100:1 | 125:1 | 150:1 | 150:1 |
| Tetrabutyltin (gms) | 2.08 | 2.08 | 1.67 | 1.39 | 1.39 |
| Pyridine (gms) | 0.04 | 0.04 | 0.03 | 0.03 | 0.03 |
| % Conversion | 74.6 | 76.1 | 72.7 | 67.5 | 63.4 |
| % Selectivity | 89.2 | 80.7 | 93.2 | 92.9 | 88.8 |

EXAMPLE XXII

The cross-metathesis of 10-undecenyl pivalate and 1-hexene was carried out in accordance with the general procedure described above. For the reaction 25.4 grams (0.1 mole) 10-undecenyl pivalate and 25.2 grams (0.3 mole) 1-hexene were reacted using a catalyst comprised of 1.59 grams (4 mmole) tungsten hexachloride, 4.17 grams (1.2 mmole) tetrabutyltin and 0.08 gram (1 mmole) pyridine. The reaction temperature was 90° C. After two hours (79.3 percent conversion) the product was analyzed and shown to contain 6.9 percent 5-decene, 16.8 percent 10-undecenyl pivalate, 35.6 percent 10-pentadecenyl pivalate and 33.3 percent 1,20-dipivaloxy-10-eicosene.

We claim:

1. A metathesis process which comprises contacting an alkenyl ester of the general formula

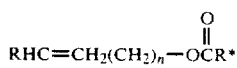

$$RHC=CH_2(CH_2)_n-OCR*$$

where R is hydrogen or an alkyl group having from 1 to 10 carbon atoms, n is an integer from 2 to 20 and R* is
(a) a tertiary alkyl group having from 4 to 20 carbon atoms of the formula

where $R_1$, $R_2$ and $R_3$ represent the same or different alkyl groups having from 1 to 9 carbon atoms, or
(b) a phenyl or substituted-phenyl group of the formula

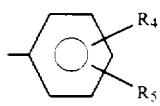

where $R_4$ and $R_5$ are hydrogen, halo or an alkyl group having from 1 to 8 carbon atoms, with a tungsten hexachloride/tetraalkyltin catalyst at a temperature from 0° C. to 220° C., said tungsten hexachloride present in an amount from 0.1 to 5 mole percent, based on the alkenyl ester, with the molar ratio of tetraalkyltin to tungsten hexachloride ranging from 0.4:1 to 6:1.

2. The process of claim 1 wherein the tetraalkyltin compound corresponds to the formula

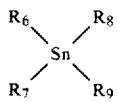

where $R_6$, $R_7$, $R_8$ and $R_9$ are alkyl groups having from 1 to 12 carbon atoms.

3. The process of claim 2 wherein the alkenyl moiety of the alkenyl ester contains from 4 to 22 carbon atoms, the tertiary alkyl group (a) contains 4 to 9 carbon atoms and for the phenyl or substituted-phenyl group (b) $R_5$ is hydrogen and $R_4$ is hydrogen, chloro, bromo or a $C_{1-4}$ alkyl group.

4. The process of claim 3 wherein the temperature is 50° C. to 150° C. and the tungsten hexachloride is present in an amount from 0.25 to 3 mole percent, based on the alkenyl ester.

5. The process of claim 4 wherein the alkenyl ester is an Ω-alkenyl ester where R is hydrogen and n is an integer from 6 to 16.

6. The process of claim 5 wherein the tetraalkyltin compound is tetrabutyl tin and the mole ratio of tetrabutyltin to tungsten hexachloride is 1:1 to 4:1.

7. The process of claim 6 which is conducted at atmospheric pressure.

8. The process of claim 1 wherein a nitrogeneous or trivalent phosphorous modifying agent is employed with the tungsten hexachloride/tetraalkyltin catalyst, the mole ratio of said modifier to tungsten hexachloride ranging from 0.01:1 to 0.75:1.

9. The process of claim 8 wherein the tetraalkyltin compound corresponds to the formula

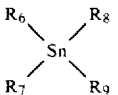

wherein $R_6$, $R_7$, $R_8$ and $R_9$ are alkyl groups having from 1 to 4 carbon atoms.

10. The process of claim 9 wherein the alkenyl moiety of the alkenyl ester contains from 4 to 22 carbon atoms, the tertiary alkyl group (a) contains 4 to 9 carbon atoms and for the phenyl or substituted-phenyl group (b) $R_5$ is hydrogen and $R_4$ is hydrogen, chloro, bromo or a $C_{1-4}$ alkyl group.

11. The process of claim 3 wherein the temperature is 50° C. to 150° C., the modifier is pyridine, tungsten hexachloride is present in an amount from 0.25 to 3 mole percent, based on the alkenyl ester, and the mole ratio of pyridine to tungsten hexachloride is 0.1:1 to 0.5:1.

12. The process of claim 11 wherein the alkenyl ester is an Ω-alkenyl ester where R is hydrogen and n is an integer from 6 to 16.

13. The process of claim 12 wherein the tetraalkyltin compound is tetrabutyl tin and the mole ratio of tetrabutyltin to tungsten hexachloride is 1:1 to 4:1.

14. A metathesis process which comprises contacting at atmospheric pressure and temperature of 50° C. to 150° C. an Ω-alkenyl ester of the formula

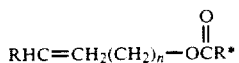

wherein R is hydrogen, n is an integer from 6 to 16 and R* is t-butyl or phenyl, with 0.25 to 3 mole percent, based on the Ω-alkenyl ester, with a catalyst consisting of tungsten hexachloride, tetrabutyl tin and pyridine, the molar ratio of tetrabutyltin to tungsten hexachloride ranging from 1:1 to 4:1 and the molar ratio of pyridine to tungsten hexachloride ranging from 0.1:1 to 0.5:1.

15. A process for cross-metathesizing an alkenyl ester and an alkene which comprises contacting the alkenyl ester and alkene at a temperature of 0° C. to 220° C. with 0.1 to 5 mole percent tungsten hexachloride, based on the alkenyl ester, and a tetraalkyltin compound, the molar ratio of tetraalkyltin to tungsten hexachloride ranging from 0.4:1 to 6:1, said alkenyl ester having the general formula

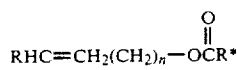

where R is hydrogen or an alkyl group having from 1 to 10 carbon atoms, n is an integer from 2 to 20 and R* is (a) a tertiary alkyl group having from 4 to 20 carbon atoms of the formula

where $R_1$, $R_2$ and $R_3$ represent the same or different alkyl groups having from 1 to 9 carbon atoms, or (b) a phenyl or substituted-phenyl group of the formula

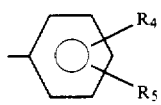

where $R_4$ and $R_5$ are hydrogen, halo or an alkyl group having from 1 to 8 carbon atoms, said alkene contains from 3 up to 50 carbon atoms and corresponds to the formula

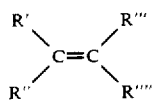

where R' is an alkyl group having from 1 to 40 carbon atoms, a $C_{3-6}$ cycloalkyl or alkyl-substituted cylcoalkyl having from 4 to 20 carbon atoms, phenyl or alkyl-substituted phenyl having from 7 to 20 carbon atoms or a radical of the formula

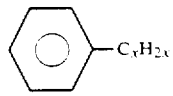

where x is an integer from 1 to 20, R''', R'''' and R'''' are hydrogen or a radical as defined for R'.

16. The process of claim 15 which is conducted at a temperature of 50° C. to 150° C. and wherein the tungsten hexachloride is present in an amount from 0.25 to 3 mole percent, based on the alkenyl ester, and the tetraalkyltin compound corresponds to the formula

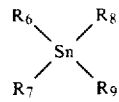

where $R_6$, $R_7$, $R_8$ and $R_9$ are alkyl groups having from 1 to 12 carbon atoms.

17. The process of claim 16 wherein the alkenyl ester is an Ω-alkenyl ester of the formula

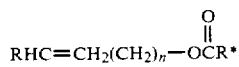

where R is hydrogen, n is an integer from 6 to 16, and R* is a tertiary alkyl group containing 4 to 9 carbon atoms or phenyl or substituted-phenyl group wherein $R_5$ is hydrogen and $R_4$ is hydrogen, chloro, bromo or a $C_{1-4}$ alkyl group.

18. The process of claim 17 wherein the alkene is an α-olefin of the formula R'HC=CH$_2$ where R' is an alkyl group having from 4 to 16 carbon atoms.

19. The process of claim 18 wherein the mole ratio of tetraalkyltin to tungsten hexachloride is 1:1 to 4:1 and $R_6$, $R_7$, $R_8$ and $R_9$ are $C_{1-4}$ alkyl groups.

20. The process of claim 19 which is conducted at atmospheric pressure and wherein the tetraalkyltin compound is tetrabutyltin.

21. The process of claim 15 wherein a nitrogeneous or trivalent phosphorous modifying agent is employed with the tungsten hexachloride and tetraalkyltin compound and the molar ratio of said modifier to tungsten hexachloride is from 0.01:1 to 0.75:1.

22. The process of claim 21 which is carried out at a temperature of 50° C. to 150° C. and wherein the tungsten hexachloride is present in an amount from 0.25 to 3 mole percent based on the alkenyl ester.

23. The process of claim 22 wherein the alkenyl ester is an Ω-alkenyl ester of the formula

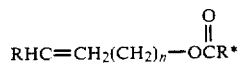

where R is hydrogen, n is an integer from 6 to 16 and R* is a tertiary alkyl group containing from 4 to 9 carbon atoms or phenyl or substituted-phenyl group wherein $R_5$ is hydrogen and $R_4$ is hydrogen, chloro, bromo, or a $C_{1-4}$ alkyl group and the alkene is an α-olefin of the formula R'HC=CH$_2$ where R' is an alkyl group having from 4 to 16 carbon atoms.

24. The process of claim 23 wherein the modifier is pyridine, the tetraalkyltin compound corresponds to the formula

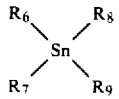

where $R_6$, $R_7$, $R_8$ and $R_9$ are alkyl groups having from 1 to 4 carbon atoms and the mole ratio of tetraalkyltin to tungsten hexachloride is 1:1 to 4:1.

25. The process of claim 24 wherein the tetraalkyltin compound is tetrabutyltin.

26. A cross-metathesis process which comprises contacting at atmospheric pressure and temperature of 50° C. to 150° C. an Ω-alkenyl ester of the formula

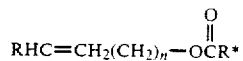

wherein R is hydrogen, n is an integer from 6 to 16 and R* is t-butyl or phenyl and an α-olefin of the formula R'HC=CH$_2$ where R' is an alkyl group having from 4 to 16 carbon atoms with a catalyst consisting of tungsten hexachloride, tetrabutyltin and pyridine, the molar ratio of tetrabutyltin to tungsten hexachloride ranging from 1:4 to 4:1 and the molar ratio of pyridine to tungsten hexachloride ranging from 0.1:1 to 0.5:1.

* * * * *

UNITED STATES PATENT AND TRADEMARK OFFICE
CERTIFICATE OF CORRECTION

PATENT NO. : 4,496,758
DATED : January 29, 1985
INVENTOR(S) : C. W. Blewett and M. D. Sublett It is certified that error appears in the above-identified patent and that said Letters Patent are hereby corrected as shown below:

In the Abstract, line 8, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

Column 1, line 23, "methyl undecenate" should read --- methyl 10-undecenoate ---; line 39, "4-acetoxy-1-butane" should read --- 4-acetoxy-1-butene ---.

Column 2, line 36, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

Column 3, line 36, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

UNITED STATES PATENT AND TRADEMARK OFFICE
CERTIFICATE OF CORRECTION

PATENT NO. : 4,496,758

DATED : January 29, 1985

INVENTOR(S) : C. W. Blewett and M. D. Sublett

It is certified that error appears in the above-identified patent and that said Letters Patent are hereby corrected as shown below:

Column 4, line 2, the formula "$RHC=CH_2(CH_2)_n$" should read --- $RHC=CH(CH_2)_n$ ---; line 13, the formula "$RHC=CH_2(CH_2)_nOH$" should read --- $RHC=CH(CH_2)_nOH$ ---.

Column 6, line 22, delete the "." after "compound".

Column 7, line 20, "if" should read --- is ---.

Column 11, line 46, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

Column 13, line 10, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---; line 30, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

Column 14, line 28, the formula "$RHC=CH_2(CH_2)_n-O\overset{O}{\overset{\|}{C}}R*$" should read --- $RHC=CH(CH_2)_n-O\overset{O}{\overset{\|}{C}}R*$; line 60, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

UNITED STATES PATENT AND TRADEMARK OFFICE
CERTIFICATE OF CORRECTION

PATENT NO. : 4,496,758

DATED : January 29, 1985

INVENTOR(S) : C. W. Blewett and M. D. Sublett

It is certified that error appears in the above-identified patent and that said Letters Patent are hereby corrected as shown below:

Column 16, line 7, the formula "$RHC=CH_2(CH_2)_n-O\overset{O}{\overset{\|}{C}}R*$" should read --- $RHC=CH(CH_2)_n-O\overset{O}{\overset{\|}{C}}R*$ ---.

Signed and Sealed this

Twenty-sixth Day of November 1985

[SEAL]

Attest:

DONALD J. QUIGG

Attesting Officer     *Commissioner of Patents and Trademarks*